(12) United States Patent
Jang et al.

(10) Patent No.: US 10,392,403 B2
(45) Date of Patent: Aug. 27, 2019

(54) PROCESS FOR PREPARING THIENOPYRIMIDINE COMPOUND AND INTERMEDIATES USED THEREIN

(71) Applicant: HANMI PHARM. CO., LTD., Hwaseong-si, Gyeonggi-do (KR)

(72) Inventors: Wook Jang, Hwaseong-si (KR); Young Ho Moon, Hwaseong-si (KR); Tae Hee Ha, Hwaseong-si (KR); Kwee Hyun Suh, Hwaseong-si (KR)

(73) Assignee: HANMI PHARM. CO., LTD., Hwaseongi-si (KR)

( * ) Notice: Subject to any disclaimer, the term of this patent is extended or adjusted under 35 U.S.C. 154(b) by 0 days.

(21) Appl. No.: 15/770,794

(22) PCT Filed: Oct. 31, 2016

(86) PCT No.: PCT/KR2016/012335
§ 371 (c)(1),
(2) Date: Apr. 25, 2018

(87) PCT Pub. No.: WO2017/074147
PCT Pub. Date: May 4, 2017

(65) Prior Publication Data
US 2018/0312520 A1    Nov. 1, 2018

(30) Foreign Application Priority Data
Oct. 30, 2015   (KR) .................. 10-2015-0151993

(51) Int. Cl.
| | | |
|---|---|---|
| C07D 495/04 | (2006.01) | |
| A61K 31/497 | (2006.01) | |
| A61K 31/519 | (2006.01) | |
| A61P 35/00 | (2006.01) | |

(52) U.S. Cl.
CPC .......... *C07D 495/04* (2013.01); *A61K 31/497* (2013.01); *A61K 31/519* (2013.01); *A61P 35/00* (2018.01)

(58) Field of Classification Search
CPC .................................................. C07D 495/04
See application file for complete search history.

(56) References Cited

U.S. PATENT DOCUMENTS

| | | | | |
|---|---|---|---|---|
| 6,245,759 | B1 | 6/2001 | Bilodeau et al. | |
| 8,957,065 | B2 * | 2/2015 | Cha .................... | C07D 491/048 |
| | | | | 514/210.21 |
| 9,345,719 | B2 * | 5/2016 | Cha .................... | C07D 491/048 |
| 10,040,801 | B2 * | 8/2018 | Baek .................... | C07D 495/04 |
| 10,160,770 | B2 * | 12/2018 | Baek .................... | C07D 495/04 |
| 2012/0065233 | A1 | 3/2012 | Gregor | |
| 2013/0116213 | A1 * | 5/2013 | Cha .................... | C07D 491/048 |
| | | | | 514/81 |
| 2015/0045324 | A1 * | 2/2015 | Cha .................... | C07D 491/048 |
| | | | | 514/81 |
| 2017/0369504 | A1 * | 12/2017 | Baek .................... | C07D 495/04 |
| 2018/0312521 | A1 * | 11/2018 | Baek .................... | C07D 495/04 |
| 2019/0016733 | A1 * | 1/2019 | Jung .................... | C07D 495/04 |

FOREIGN PATENT DOCUMENTS

| | | | | |
|---|---|---|---|---|
| CN | 201510872331 | * | 2/2015 | .......... A61K 31/519 |
| KR | 10-2014-0118575 A | | 10/2014 | |
| WO | 2011162515 A2 | | 12/2011 | |
| WO | WO-2011162515 A2 | * | 12/2011 | .......... C07D 491/048 |
| WO | 2016/108623 A1 | | 7/2016 | |
| WO | WO-2016108623 A1 | * | 7/2016 | .......... C07D 495/04 |
| WO | WO-2017092523 A1 | * | 6/2017 | .......... A61K 31/519 |

OTHER PUBLICATIONS

Manisha S. Phoujdar et al., "Microwave-based synthesis of novel thienopyrimidine bioisosteres of gefitinib", Tetrahedron Letters, 2008, pp. 1269-1273, vol. 49.
International Search Report of PCT/KR2016/012335 dated Feb. 7, 2017 [PCT/ISA/210].
Written Opinion of PCT/KR2016/012335 dated Feb. 7, 2017 [PCT/ISA/237].
European Patent Office; Communication dated Feb. 25, 2019 issued in counterpart application No. 16860330.6.

* cited by examiner

*Primary Examiner* — Alexander R Pagano
(74) *Attorney, Agent, or Firm* — Sughrue Mion, PLLC

(57) ABSTRACT

The present invention relates to a novel method for preparing thienopyrimidine compound having an activity of selectively inhibiting tyrosine kinase, specifically the mutant epidermal growth factor receptor tyrosine kinase; and a novel intermediate used therein. According to the method of the present invention, the industrial mass-production of the compound of Formula 1, which is useful as a therapeutic agent for non-small cell lung cancer induced by the mutant epidermal growth factor receptor tyrosine kinase, can be implemented more conveniently and efficiently than the conventional technology.

17 Claims, No Drawings

PROCESS FOR PREPARING THIENOPYRIMIDINE COMPOUND AND INTERMEDIATES USED THEREIN

TECHNICAL FIELD

The present invention relates to a novel method for preparing thienopyrimidine compound having an activity of selectively inhibiting tyrosine kinase, specifically the mutant epidermal growth factor receptor tyrosine kinase; and a novel intermediate used therein.

BACKGROUND ART

U.S. Pat. No. 8,957,065 discloses a thienopyrimidine compound having an activity of selectively inhibiting the mutant epidermal growth factor receptor tyrosine kinase, represented by the following Formula 1:

[Formula 1]

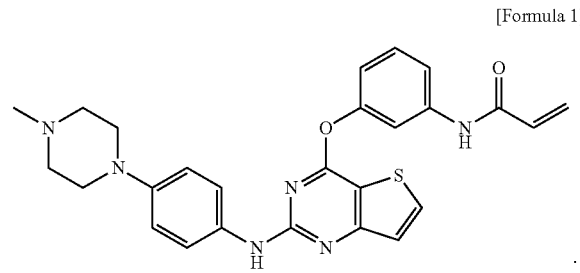

Also, the above document discloses a method for preparing the compound of Formula 1. Specifically, as illustrated in Scheme 1 below, the method comprises reacting 2,4-dichlorothieno[3,2-d]pyrimidine of Formula 3 with 3-nitrophenol to prepare the compound of Formula B; reacting the compound of Formula B with 4-(4-methylpiperazin-1-yl)aniline to prepare the compound of Formula C; then reducing the nitro group of the compound of Formula C to prepare the compound of Formula D; and reacting the compound of Formula D with acryloyl chloride to prepare the compound of Formula 1.

[Scheme 1]

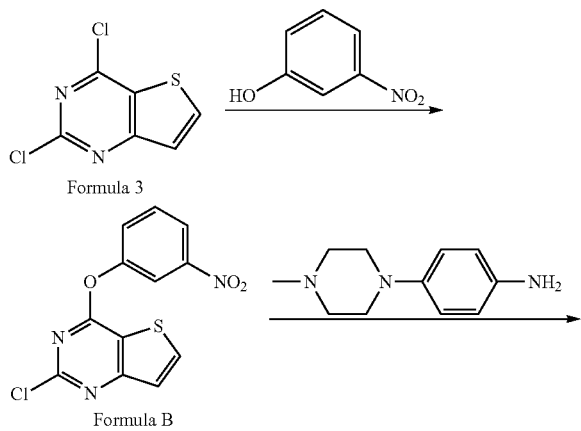

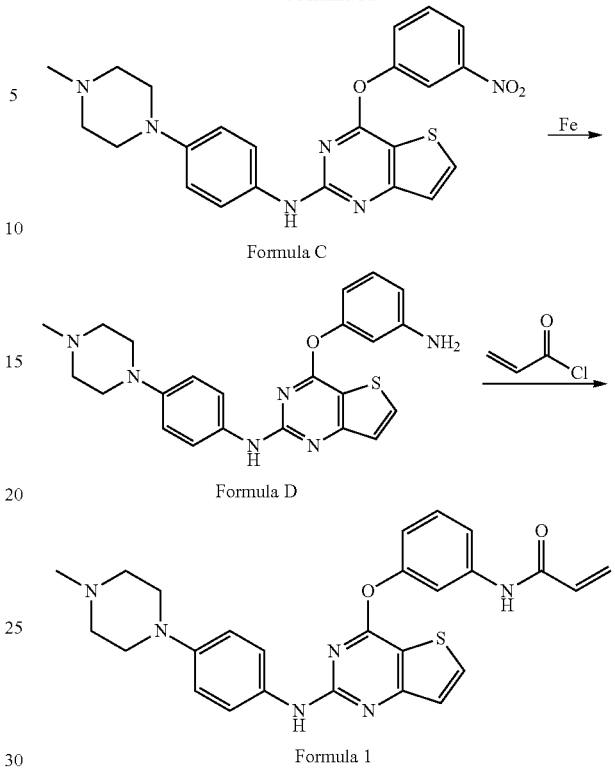

However, the synthesis of the compound in accordance with Scheme 1 has several problems, as explained below. In order to remove impurities generated in the step of obtaining the compound of Formula C, a column chromatography purification method was used, but the method is not suitable for industrial production, giving a low yield. Further, an excess amount of iron is required for reducing the nitro group of the compound of Formula C, and the compound of Formula D thus obtained is reacted with acryloyl chloride, which is hard to handle. In addition, the compounds of Formula D and Formula 1 both need to be purified by using a column chromatography, which is difficult to apply to the industrial production.

Thus, the present inventors have accomplished the present invention by developing a novel method for preparing a thienopyrimidine compound, which allows the easy preparation of the compound in an efficient and industrially applicable way.

PRIOR ART DOCUMENT

Patent Document

Patent Document 1: U.S. Pat. No. 8,957,065.

DISCLOSURE

Technical Problem

Therefore, it is an object of the present invention to provide a convenient and efficient method for preparing a thienopyrimidine compound.

It is another object of the present invention to provide an intermediate used for preparing the thienopyrimidine compound.

Technical Solution

In accordance with one object of the present invention, there is provided a method for preparing the compound of Formula 1, comprising steps of:

1) subjecting the compound of Formula 3 to a reaction with the compound of Formula 4 in an organic solvent under the presence of a base to obtain the compound of Formula 2; and
2) subjecting the compound of Formula 2 to a reaction with the compound of Formula 5 in an organic solvent under the presence of an acid to obtain the compound of Formula 1:

[Formula 1]

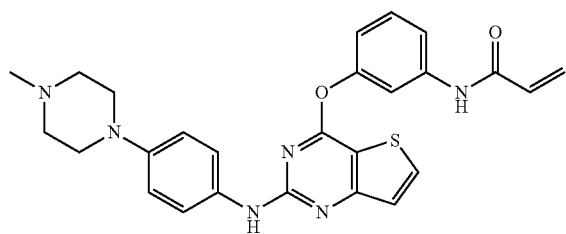

[Formula 2]

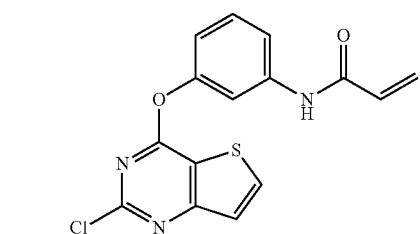

[Formula 3]

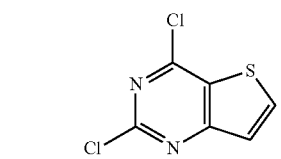

[Formula 4]

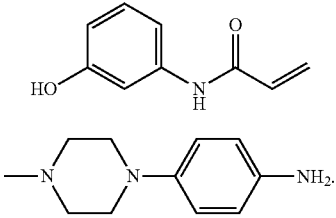

[Formula 5]

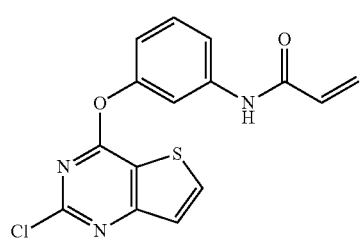

In accordance with another object of the present invention, there is provided the compound of Formula 2 below.

[Formula 2]

Using the method of the present invention, the industrial mass-production of the compound of Formula 1, which is useful as a therapeutic agent for non-small cell lung cancer induced by the mutant epidermal growth factor receptor tyrosine kinase, can be implemented more conveniently and efficiently than the conventional technology.

MODE FOR INVENTION

Hereinafter, the present invention will be described in detail.

The present invention provides a method for preparing the compound of Formula 1, comprising steps of:

1) subjecting the compound of Formula 3 to a reaction with the compound of Formula 4 in an organic solvent under the presence of a base to obtain the compound of Formula 2; and
2) subjecting the compound of Formula 2 to a reaction with the compound of Formula 5 in an organic solvent under the presence of an acid to obtain the compound of Formula 1:

[Formula 1]

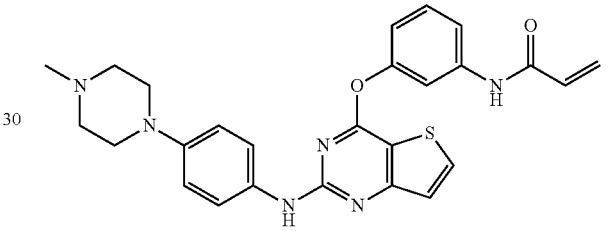

[Formula 2]

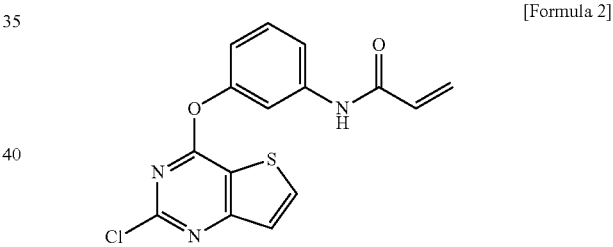

[Formula 3]

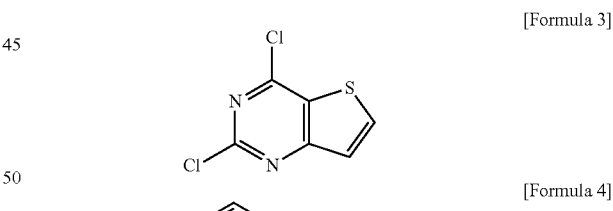

[Formula 4]

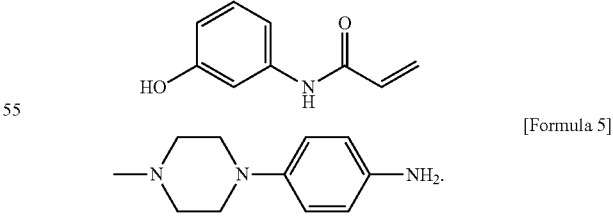

[Formula 5]

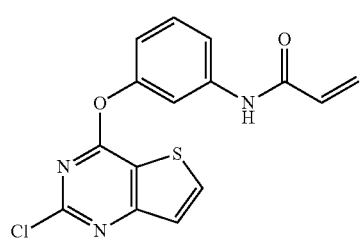

The present invention provides step 1) of subjecting the compound of Formula 3 to a reaction with the compound of Formula 4 in an organic solvent under the presence of a base to obtain the compound of Formula 2.

In the step of preparing the compound of Formula 2, the compound of Formula 4, which is subjected to a reaction with the compound of Formula 3, may be used in an amount of 1.0 to 1.5 molar equivalents, specifically 1.2 to 1.3 molar equivalents based on 1 molar equivalent of the compound of Formula 3.

The organic solvent used in step 1) may be selected from the group consisting of acetonitrile, acetone, methyl ethyl ketone, methyl isobutyl ketone, methyl acetate, ethyl acetate, isopropyl acetate, N',N'-dimethylformamide, N',N-dimethylacetamide, dimethylsulfoxide, and a mixture thereof. According to one embodiment of the present invention, the organic solvent may be N',N'-dimethylformamide, N',N-dimethylacetamide, or dimethylsulfoxide. The amount of the organic solvent used may be 5 to 20 mL, specifically 10 to 15 mL, based on 1 g of the compound of Formula 3. The reaction may be carried out at 10° C. to 60° C., specifically at 20° C. to 35° C., for 3 to 30 hours, specifically for 4 to 24 hours.

In addition, the base used in the above reaction may be potassium carbonate, calcium carbonate, sodium carbonate, potassium hydroxide, sodium hydroxide, sodium hydrogen carbonate or a mixture thereof. According to one embodiment of the present invention, the base may be potassium carbonate or sodium carbonate. The amount of the base used in the reaction may be 1.0 to 5.0 molar equivalents, specifically 2.0 to 3.0 molar equivalents based on 1 molar equivalent of the compound of Formula 3.

The compound of Formula 2 produced in the above reaction may be obtained by adding a mixed solvent of an organic solvent and water to the resulting solution containing the compound of Formula 2 to precipitate the compound as a solid.

The organic solvent used for the precipitation of the compound of Formula 2 may be acetone, methanol, ethanol, isopropanol, acetonitrile or a mixture thereof. According to one embodiment of the present invention, the organic solvent may be acetone or isopropanol.

The organic solvent may be used as a mixture with water, and the mixing ratio may vary depending on the type of the organic solvent. According to one embodiment of the present invention, when acetone or isopropanol is used as an organic solvent, the organic solvent may be mixed with water in a volume ratio of 3:1 to 1:3, specifically 2:1 to 1:2. According to one embodiment of the present invention, the mixing ratio may be 1:1.

In addition, the present invention may further comprise a step of improving the purity of the compound of Formula 2 obtained in the above step. In order to improve the purity, either or both of the two methods described below may be used.

In the first method, the compound of Formula 2 obtained is additionally purified by adding a mixed solvent of an organic solvent and water to the compound of Formula 2; heating the resulting mixture to the reflux temperature of the solvent while stirring; cooling the mixture to the room temperature (RT); and then filtering and drying the re-precipitated solid, in order to obtain the compound of Formula 2 with an improved purity.

The second method is conducted prior to adding a mixed solvent of an organic solvent and water to precipitate the compound of Formula 2 as a solid, the method comprising: adding an organic solvent to the reaction solution obtained after the reaction of the compound of Formula 4 with the compound of Formula 3; heating the resulting mixture; filtering and removing insoluble substances produced; adding an organic solvent to the filtrate; and cooling the resulting mixture, and then the compound of Formula 2 with an improved purity can be obtained through the subsequent precipitation procedure as described above.

The organic solvent which can be used in the step of improving the purity is the same as that used for the precipitation of the compound, and the organic solvent may be used alone or in a mixture with water. The mixing ratio of the organic solvent and water may vary depending on the type of the organic solvent.

The present invention provides step 2) of subjecting the compound of Formula 2 to a reaction with the compound of Formula 5 in an organic solvent under the presence of an acid to obtain the compound of Formula 1 as below.

In the step of preparing the compound of Formula 1, the compound of Formula 5 which reacts with the compound of Formula 2 may be used in an amount of 1.0 to 2.0 molar equivalents, specifically 1.3 to 1.7 molar equivalents based on 1 molar equivalent of the compound of Formula 2.

The organic solvent used in step 2) may be selected from the group consisting of tetrahydrofuran, dioxane, acetonitrile, methanol, ethanol, butanol, 2-butanol, isopropanol, N',N-dimethylformamide, N',N-dimethylacetamide, dimethylsulfoxide, and a mixture thereof. The amount of the organic solvent used may be 5 to 20 mL, specifically 10 to 15 mL based on 1 g of the compound of Formula 2. The reaction may be carried out at 60° C. to 120° C., specifically at 80° C. to 100° C., for 1 to 15 hours, specifically for 2 to 12 hours.

Also, the acid used in the reaction may be an inorganic or organic acid. For example, the inorganic acid may be hydrochloric acid, nitric acid, sulfuric acid, etc., and the organic acid may be benzoic acid, toluene, sulfonic acid, benzene sulfonic acid, methane sulfonic acid, acetic acid, trifluoroacetic acid, etc. According to one embodiment of the present invention, the acid may be acetic acid or trifluoroacetic acid. The amount of the acid used in the reaction may be 2.0 to 5.0 molar equivalents, specifically 3.0 to 4.0 molar equivalents based on 1 molar equivalent of the compound of Formula 2.

The preparation method of the present invention may further comprise a step of separating the organic solvent layer containing the compound of Formula 1, following the above reaction.

To separate the organic solvent layer, upon the completion of the reaction, the reaction solution is cooled to RT, then an organic solvent or a mixed solvent of an organic solvent and water is added to the reaction solution, and the pH thereof is adjusted.

The organic solvent that can be used for the separation of the organic solvent layer may be chloroform, dichloromethane or a mixture thereof. The organic solvent may be used alone or in a mixture with water, and the mixing ratio of the organic solvent and water may vary depending on the type of the organic solvent. According to one embodiment of the present invention, when chloroform or dichloromethane is used as an organic solvent, the organic solvent may be mixed with water in a volume ratio of 1:1 to 1:5, specifically 1:1.5 to 1:3. Also, the pH may be adjusted to pH 2.0 to 5.0, specifically pH 3.0 to 4.0. To adjust the pH, an aqueous solution containing sodium hydrogen carbonate, sodium carbonate, and potassium carbonate, etc. may be used. The step of separating the organic solvent layer may be repeated once or more, specifically 1 to 3 times.

The compound of Formula 1 produced by the above reaction can be obtained to precipitate the compound as a solid by adding an organic solvent to the reaction solution. The same organic solvent used for the precipitation of Formula 2 can be used for the precipitation of the compound of Formula 1.

The organic solvent may be used in a mixture with water, and the mixing ratio of the organic solvent and water may vary depending on the type of the organic solvent. According to one embodiment of the present invention, when acetone or isopropanol is used as an organic solvent, the organic solvent may be mixed with water in a volume ratio of 1:3 to 1:9, specifically 1:3 to 1:6. According to one embodiment of the present invention, the organic solvent may be mixed with water in a volume ratio of 1:3 or 1:6.

In addition, the present invention may further comprise a step of improving the purity of the compound of Formula 1 obtained in the above step.

The compound of Formula 1 with an improved purity may be obtained by re-precipitating the compound of Formula 1 produced above in a mixed solvent of an organic solvent and water; heating the resulting mixture to the reflux temperature of the solvent to dissolve the compound; cooling the mixture to RT; and then filtering and drying the re-precipitated solid.

The organic solvent for the re-precipitation may be used alone or as a mixture with water. Examples of the organic solvents may include acetone, methanol, ethanol, isopropanol, acetonitrile and the like. According to one embodiment of the present invention, the organic solvent may be acetone or isopropanol. When using the organic solvent as a mixture with water, the mixing ratio of the organic solvent and water may vary depending on the type of the organic solvent. According to one embodiment of the present invention, when acetone or isopropanol is used as an organic solvent, the organic solvent may be mixed with water in a volume ratio of 8:1 to 2:1, specifically 5:1 to 3:1. According to one embodiment of the present invention, the organic solvent may be mixed with water in a volume ratio of 4:1.

The reaction for the dissolution of the compound may be carried out at or above 50° C., specifically at a temperature of from 50° C. to the reflux temperature of the solvent, for 0.5 to 3 hours, specifically for 1 to 2 hours. In addition, the cooling for re-precipitation may be carried out at or below RT, specifically at a temperature of from 5° C. to RT, for 2 to 10 hours, specifically for 3 to 5 hours. The re-precipitation can be carried out at least once, specifically at least twice.

The compound of Formula 3 used as a starting material in the above step, and the compounds of Formula 4 and Formula 5 (reactants added in each step) are commercially available or prepared according to the conventional methods.

In addition, the present invention provides the compound of Formula 2:

[Formula 2]

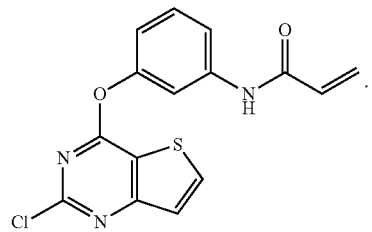

The following Examples are intended to further illustrate the present invention without limiting its scope.

Example 1. Preparation of N-(3-((2-((4-(4-methyl-piperazin-1-yl)phenyl)amino)thieno[3,2-d]pyrimidin-4-yl)oxy)phenyl) acrylamide (Formula 1)-1

1.1. Preparation of N-(3-((2-chlorothieno[3,2-d]pyrimidin-4 yl)oxy)phenyl) acrylamide (Formula 2)

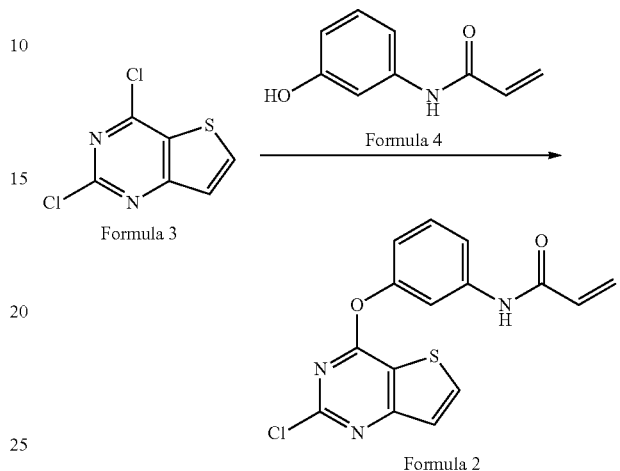

125.5 g (0.61 mol) of 2,4-dichlorothieno[3,2-d]pyrimidine (Formula 3) and 110.0 g (0.67 mol) of N-(3-hydroxyphenyl)acrylamide (Formula 4) were added to 1.5 L of dimethyl sulfoxide. 169.4 g (1.23 mol) of potassium carbonate was added thereto and stirred at RT for 24 hours. To the resulting solution, a mixed solvent of 750 mL of water and 750 mL of acetone was added slowly, followed by stirring at RT for 2 hours, and then the precipitated solid was filtered. The filtered solid was washed with 200 mL of water, and dried to give 197.0 g of the title compound (yield: 97.0%, HPLC purity 93.5%).

A mixed solvent of 3.2 L of water and 800 mL of methanol was added to the title compound thus obtained, which was then heated at 100° C. for 1 hour under reflux. After completion of the reaction, the temperature of the reaction solution was lowered to RT, and then the solid thus produced was filtered and washed with 400 mL of water. The resultant was dried at 50° C. to give 165.3 g of the title compound (yield: 83.9%, HPLC purity 98.7%).

Melting point: 233° C. to 235° C.
MS spectrum: m/z=332.05 (M+1).
$^1$H-NMR spectrum (300 MHz, DMSO-$d_6$) δ 10.46 (s, 1H), 8.57 (d, 1H), 7.80 (d, 1H), 7.65 (s, 1H), 7.56 (d, 1H), 7.47 (t, 1H), 7.12-7.09 (m, 1H), 6.46 (dd, 1H), 6.27 (dd, 1H), 5.79 (dd, 1H).

1.2. Preparation of N-(3-((2-((4-(4-methylpiperazin-1-yl)phenyl)amino)thieno[3,2-d]pyrimidin-4-yl)oxy)phenyl)acrylamide (Formula 1)

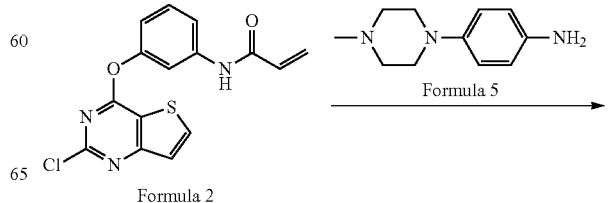

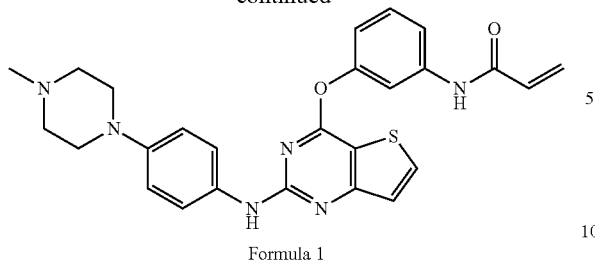

Formula 1

100.0 g (0.30 mol) of N-(3-((2-chlorothieno[3,2-d]pyrimidin-4-yl)oxy)phenyl)acrylamide (Formula 2) and 86.5 g (0.45 mol) of 4-(4-methylpiperazin-1-yl)aniline (Formula 5) were added to 1.0 L of N',N'-dimethyl-acetamide. 67.2 mL (0.90 mol) of trifluoroacetic acid was added thereto slowly, and stirred at 90° C. for 12 hours. The temperature of the reaction solution was lowered to 35° C., and a mixed solvent of 500 mL of chloroform and 1.0 L of water was added thereto. After adjusting the pH of the solution to 3.0 with a saturated aqueous solution of sodium hydrogen carbonate, the organic solvent layer was separated, and a 500 mL mixed solvent of chloroform and water (volume ratio 3:1) was added to the water layer. The separation of the organic layer as above was repeated twice. The separated organic solvent layers were combined together and washed with 500 mL of saturated sodium bicarbonate aqueous solution and 500 mL of water. The washed organic solvent layer was dried over 200 g of anhydrous magnesium sulfate and then concentrated under a reduced pressure at 40° C. To the residue thus obtained, 500 mL of isopropanol was added, which was concentrated again under a reduced pressure at 40° C. The resultant was added with 400 mL of isopropanol again, added with 2.5 L of water dropwise slowly, and stirred at RT for 24 hours. Then the solid thus obtained was filtered. The filtered solid was washed with water, and dried at 50° C. to give 85.0 g of a crude product of the title compound (yield 57.9%, HPLC purity 96.0%).

85.0 g of the crude product of the title compound thus obtained was added to a mixed solvent of 850 mL of acetone and water (volume ratio 4:1) and dissolved therein by heating at 65° C. for one hour. Then, the resultant was cooled slowly and stirred for 5 hours to give a solid. The solid thus obtained was filtered and washed with a 85 mL mixed solvent of acetone and water (volume ratio 4:1) cooled to 10° C. or lower, and subsequently with a 170 mL mixed solvent of acetone and water (volume ratio 1:1). The obtained solid was dried at 50° C. for 24 hours to give 63.3 g of a first purified title compound (yield 74.5%, HPLC purity 98.3%).

60.0 g of the title compound thus obtained after the first purification was purified again with a 900 mL mixed solvent of acetone and water (volume ratio 4:1) by the same method described above for the first purification, to give the second purified title compound (yield: 84.3%, HPLC purity 99.1%).

Melting point: 204° C. to 205° C.

MS spectrum: m/z=487.19 (M+1).

$^1$H-NMR spectrum (300 MHz, DMSO-d6) δ 10.37 (s, 1H), 9.24 (s, 1H), 8.27 (d, 1H), 7.71 (d, 1H), 7.64 (d, 1H), 7.49-7.41 (m, 3H), 7.32 (d, 1H), 7.07 (dd, 1H), 6.71 (d, 2H), 6.42 (dd, 1H), 6.28 (dd, 1H), 5.78 (dd, 1H), 2.99 (t, 4H), 2.43 (t, 4H), 2.21 (s, 3H).

Example 2. Preparation of N-(3-((2-((4-(4-methyl-piperazin-1-yl)phenyl)amino)thieno[3,2-d]pyrimidin-4-yl)oxy)phenyl) acrylamide (Formula 1)-2

2.1. Preparation of N-(3-((2-chlorothieno[3,2-d]pyrimidin-4-yl)oxy)phenyl)acrylamide (Formula 2)

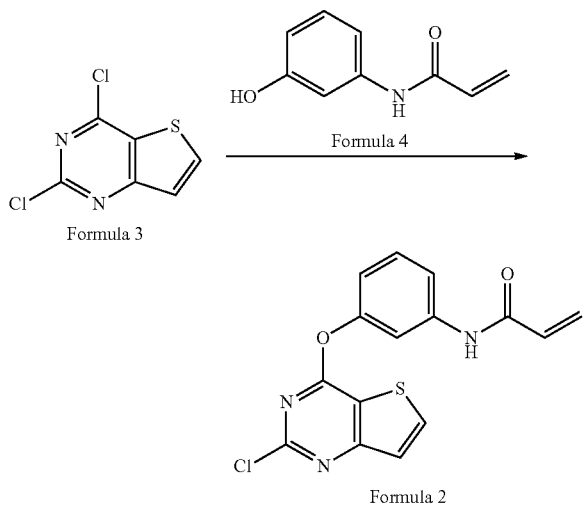

125.5 g (0.61 mol) of 2,4-dichlorothieno-[3,2-d]pyrimidine (Formula 3) and 110.0 g (0.67 mol) of N-(3-hydroxyphenyl)acrylamide (Formula 4) were added to 1.5 L of dimethyl sulfoxide. 101.2 g (0.73 mol) of potassium carbonate was added thereto, followed by stirring at RT for 4 hours. 500 mL of acetone was added to the reaction solution, which was then heated to 50° C. and stirred for 20 minutes. Then, the reaction solution was filtered on diatomaceous earth and washed with 250 mL of acetone. The filtrate was heated to 35° C., added with 1.25 L of isopropanol, slowly cooled to RT, and stirred for 1 hour. A mixed solvent containing 500 mL of acetone and 1.0 L of water was added thereto slowly. Then the solution was stirred for 1 hour at RT, and the solid thus obtained was filtered. The filtered solid was washed with a mixed solvent of 250 mL of acetone and 500 mL of water first, and further with 250 mL of acetone. Then, the resultant was dried at 50° C. to give 176.7 g of the title compound (yield: 87.0%, HPLC purity 99.4%).

Melting point: 235° C. to 236° C.

2.2. N-(3-((2-((4-(4-methylpiperazin-1-yl)phenyl)amino)thieno[3,2-d]pyrimidin-4-yl)oxy)phenyl)acrylamide (Formula 1)

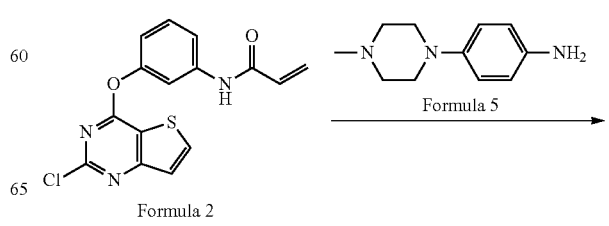

Formula 2

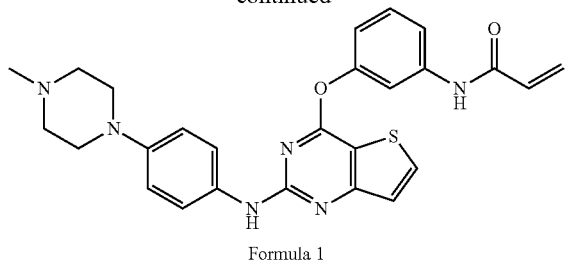

Formula 1

180.0 (0.54 mol) of N-(3-((2-chlorothieno[3,2-d]pyrimidin-4-yl)oxy)phenyl)acrylamide (Formula 2) and 155.7 g (0.81 mol) of 4-(4-methylpiperazin-1-yl)aniline (Formula 5) were added to a mixed solvent of 720 mL of N',N'-dimethylacetamide and 720 mL of isopropanol. 103 mL (1.35 mol) of trifluoroacetic acid was added thereto dropwise, followed by stirring at 90° C. for 2 hours. The reaction solution was cooled to 50° C., and then concentrated under a reduced pressure to remove isopropanol. To the residue cooled to RT, 1.8 L of water and 1.25 L of dichloromethane were added, and the pH of the solution was adjusted to 3.0 with a saturated sodium bicarbonate aqueous solution. Then, the separation of the organic solvent layer and the extraction of the water layer with 1.0 L of dichloromethane were repeated twice. The separated organic solvent layers were combined together and washed with 1.0 L of a saturated sodium bicarbonate aqueous solution, the insoluble substances were then removed by filtration, and the filtrate was concentrated under a reduced pressure. To the residue thus obtained, 400 mL of isopropanol was added, which was concentrated under a reduced pressure. Then the resultant was added with 1.5 L of isopropanol again, and added with 4.5 L of water dropwise slowly. The mixture solution was stirred at RT for 2 hours, and the solid thus obtained was washed with 720 mL of water. The washed solid was dried at 50° C. to give 216.0 g of a crude product of the title compound (yield 81.8%, HPLC purity 92.2%).

180.0 g of the crude product of the title compound obtained was added to a mixed solvent of 2.15 L of acetone and 200 mL of water and dissolved therein by heating at 60° C. for one hour. Then, the resultant was cooled to RT slowly, stirred for 3 hours, and then cooled again and stirred at 5 to 10° C. for 2 hours. The solid thus obtained was filtered and washed with a 450 mL mixed solvent of acetone and water (volume ratio 4:1), and dried at 50° C. to give 136.7 g of the first purified title compound (yield 63.3%, HPLC purity 97.8%). The first purified title compound thus obtained was purified again in a similar manner to the first purification to give 118.6 g of a second purified title compound (yield: 86.8%, HPLC purity 99.1%).

Melting point: 204° C. to 205° C.

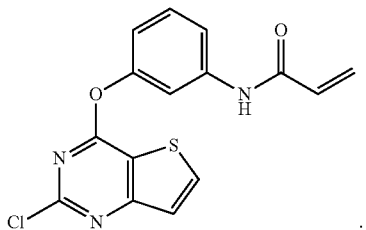

The invention claimed is:
1. A method for preparing the compound of Formula 1, comprising steps of:
   1) subjecting the compound of Formula 3 to a reaction with the compound of Formula 4 in an organic solvent under the presence of a base to obtain the compound of Formula 2; and
   2) subjecting the compound of Formula 2 to a reaction with the compound of Formula 5 in an organic solvent under the presence of an acid to obtain the compound of Formula 1:

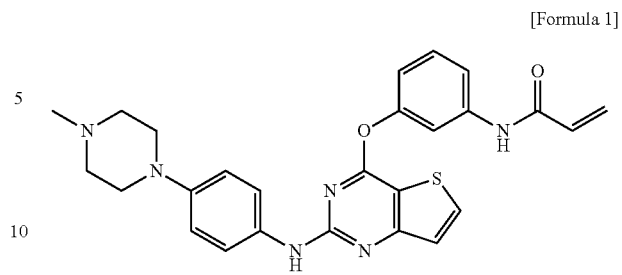

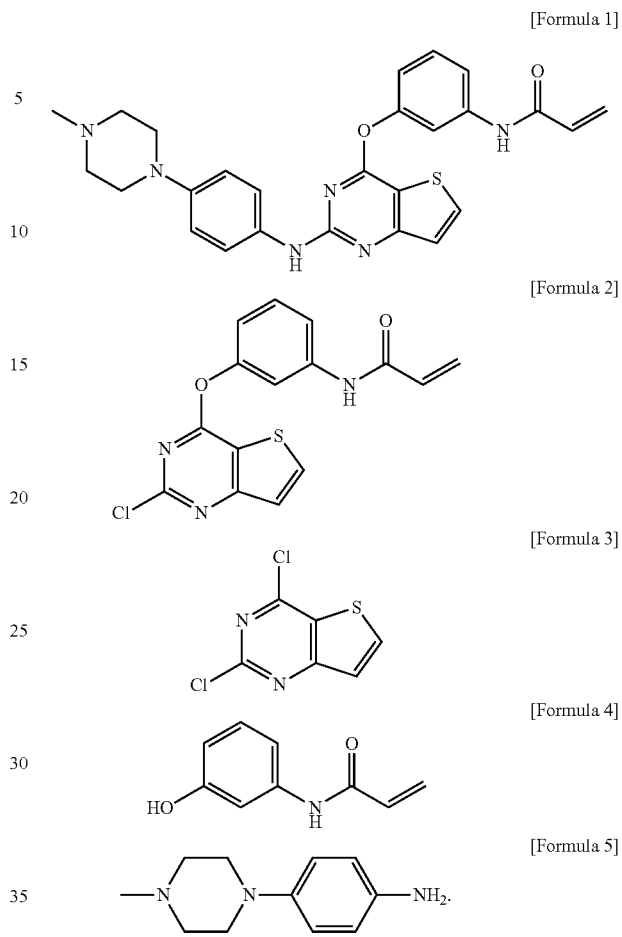

2. The method of claim 1, wherein the organic solvent used in step 1) is selected from the group consisting of acetonitrile, acetone, methyl ethyl ketone, methyl isobutyl ketone, methyl acetate, ethyl acetate, isopropyl acetate, N',N'-dimethylformamide, N',N-dimethylacetamide, dimethylsulfoxide, and a mixture thereof.

3. The method of claim 1, wherein the base is selected from the group consisting of potassium carbonate, calcium carbonate, sodium carbonate, potassium hydroxide, sodium hydroxide, sodium hydrogen carbonate, and a mixture thereof.

4. The method of claim 1, which further comprises, after step 1), the step of precipitating the compound of formula 2 obtained in step 1) in a mixed solvent of an organic solvent and water.

5. The method of claim 4, wherein the organic solvent is selected from the group consisting of acetone, methanol, ethanol, isopropanol, acetonitrile, and a mixture thereof.

6. The method of claim 5, wherein the organic solvent is acetone or isopropanol.

7. The method of claim 4, wherein the mixed solvent comprises the organic solvent and water in a volume ratio of 3:1 to 1:3.

8. The method of claim 1, wherein the organic solvent used in step 2) is selected from the group consisting of tetrahydrofuran, dioxane, acetonitrile, methanol, ethanol, butanol, 2-butanol, isopropanol, N',N-dimethylformamide, N',N'-dimethylacetamide, dimethylsulfoxide, and a mixture thereof.

9. The method of claim 1, wherein the acid is an inorganic or organic acid.

10. The method of claim 9, wherein the inorganic acid is selected from the group consisting of hydrochloric acid, nitric acid, sulfuric acid, and a mixture thereof.

11. The method of claim 9, wherein the organic acid is selected from the group consisting of benzoic acid, toluene, sulfonic acid, benzene sulfonic acid, methane sulfonic acid, acetic acid, trifluoroacetic acid, and a mixture thereof.

12. The method of claim 11, wherein the organic acid is trifluoroacetic acid.

13. The method of claim 1, which further comprises, after step 2), the step of precipitating the compound of formula 1 obtained in step 2) in a mixed solvent of an organic solvent and water.

14. The method of claim 13, wherein the organic solvent is selected from the group consisting of acetone, methanol, ethanol, isopropanol, acetonitrile, and a mixture thereof.

15. The method of claim 14, wherein the organic solvent is acetone or isopropanol.

16. The method of claim 13, wherein the mixed solvent comprises the organic solvent and water in a volume ratio of 1:3 to 1:9.

17. The compound of Formula 2:

[Formula 2]